United States Patent

Ljungstroem

[11] Patent Number: 5,159,926
[45] Date of Patent: Nov. 3, 1992

[54] MEDICAL STIMULATION AND/OR MONITORING DEVICE INTERACTING WITH THE BODY OF A PATIENT BASED UPON SELECTABLE PARAMETER SET

[75] Inventor: Jan Ljungstroem, Solna, Sweden

[73] Assignee: Siemens Aktiengesellschaft, Munich, Fed. Rep. of Germany

[21] Appl. No.: 573,794

[22] Filed: Aug. 28, 1990

[30] Foreign Application Priority Data

Aug. 28, 1989 [EP] European Pat. Off. ......... 89115857.8

[51] Int. Cl.⁵ ............................................. A61N 1/365
[52] U.S. Cl. .............................................. 128/419 PG
[58] Field of Search ................................. 128/419 PG

[56] References Cited

U.S. PATENT DOCUMENTS

| | | | |
|---|---|---|---|
| 4,365,633 | 12/1982 | Loughman et al. | 128/419 PG |
| 4,401,120 | 8/1963 | Hartlaub et al. | 128/419 PG |
| 4,407,288 | 10/1983 | Langer et al. | 128/419 PG |
| 4,485,818 | 12/1984 | Leckrone et al. | 128/419 PG |
| 4,562,841 | 1/1986 | Brockway et al. | 128/419 PG |
| 4,922,930 | 5/1990 | Adkins et al. | 128/419 PG |

FOREIGN PATENT DOCUMENTS 0160801 11/1985 European Pat. Off. .
WO86/07270 12/1986 Italy .

Primary Examiner—William E. Kamm
Assistant Examiner—Kennedy J. Schaetzle
Attorney, Agent, or Firm—Hill, Van Santen, Steadman & Simpson

[57] ABSTRACT

A medical device interacting with the body of a patient for stimulating and/or monitoring a physiological function includes control electronics which uses a parameter set which can be fetched from a memory, the parameter set defining the interaction. A number of different parameter sets can be stored in the memory, with a switching system being provided to fetch respectively different parameter sets under differing conditions.

8 Claims, 1 Drawing Sheet

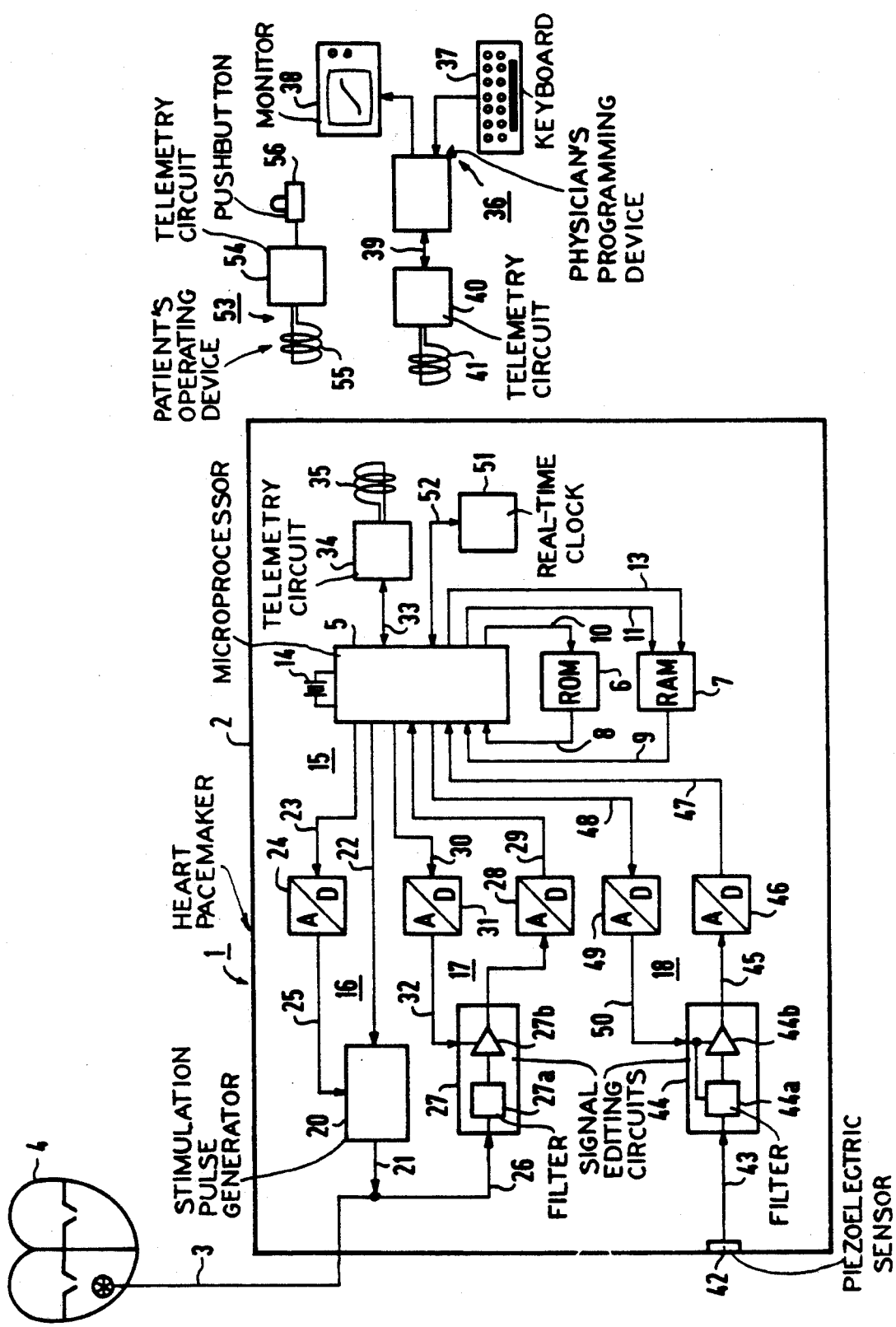

MEDICAL STIMULATION AND/OR MONITORING DEVICE INTERACTING WITH THE BODY OF A PATIENT BASED UPON SELECTABLE PARAMETER SET

BACKGROUND OF THE INVENTION

1. Field of the Invention

The present invention is directed to a medical device which interacts with the body of a patient for stimulation and/or monitoring a physiological function, wherein the interaction is defined by control electronics on the basis of a parameter set which can be fetched from a memory.

2. Description of the Prior Art

Electromedical therapy devices for electrical stimulation of muscle tissue, such as heart pacemakers, are known which interact with the body of the patient on the basis of a parameter set which is stored in a memory. Such known pacemakers include means for detecting spontaneous heart beats and means for stimulating heart muscle activity. Control electronics activates the means for stimulation to generate electrical stimulation pulses in the absence of a spontaneous heartbeat, generally so that the pacing rate does not fall below a defined, usually variable, heartbeat rate. The interaction of the pacemaker with the body of the patient can be influenced by data, known as a "parameter set", which can be stored in a memory in the pacemaker and can be fetched with the control electronics. Such data relate to the heartbeat rate which cannot be downwardly transgressed, the sensitivity of the means for detection, and the energy content of the stimulation pulses. Usually it is possible to modify the parameter set in totality, or with respect to individual data elements. In implantable pacemakers, this is accomplished in a non-invasive manner using an external programming device operating with a telemetry circuit. Such an operation is known as programming, or reprogramming. Programming or reprogramming is normally reserved for the attending physician. Because the patient only visits the attending physical between relatively long time intervals, the physical must select the data of the parameter set so as to enable a sufficient effectiveness of the heart pacemaker for the greatest requirements of the patient and for the greatest range of situations. In the best case, the programmed parameter set thus represents a successful compromise. Under these conditions, there is the need to be able to adapt the parameter set to the momentary requirements of the patient in a simple way.

SUMMARY OF THE INVENTION

It is an object of the present invention to provide a medical device which interacts with the body of a patient such that the parameter set which defines the interaction of the device with the patient can be adapted to different requirements of the patient in a simple and all-embracing manner, preferably without requiring the intervention of the attending physician.

The above object is achieved in accordance with the principles of the present invention in a medical device of the type described above wherein a plurality of parameter sets can be stored in the memory, with one of the stored parameter sets being able to be called with a switch. The control electronics can only access that parameter set which is enabled by the switch, so that the control electronics fetches the parameter set which is adapted to the momentary requirements of the patient, by means of suitable fashioning and actuation of the switch.

In a preferred embodiment of the invention, the switch includes a real-time clock with which a parameter set intended for a specific time span can be enabled for fetching dependent on the time of day. It is thus possible to store a parameter set adapted for the time of day during which the patient pursues an activity involving physical activity, for example his profession, and for storing a parameter set for nighttime adapted to the requirements of the sleeping patient, with one or the other parameter set being enabled for fetching dependent on the time of day.

In a further modification of the invention, the switch may include an operating unit which permits one of the parameter sets to be enabled for fetching. Because only selection among the stored parameter sets is possible, with no modification of the data of the parameter sets being possible, this operating unit can be operated by the patient. For example, if the patient has a sickness requiring bed rest, the patient may then select a parameter adapted to the requirements of a bedridden patient. If the device is of the type which is implantable into the body of the patient, the operating unit can be an external operating device with which one of the parameter sets ca be enabled for fetching by telemetry.

In a further embodiment of the invention, the switch enables one of the parameter sets for fetching dependent on the intensity of the physiological function of the patient. Upon the occurrence of defined, abnormal conditions, recognizable with reference to a signal corresponding to the respective physiological function, it is possible to enable a parameter set suitable for terminating the abnormal condition, or at least adapted to this condition. In the case of a heart pacemaker, for example, tachycardia, fibrillations, or the like can be recognized with respect to a signal corresponding to normal heart activity, and steps can be taken to terminate the tachycardia or to effect defibrillation.

In another embodiment of the invention, the switch enables a parameter set for fetching by exclusively enabling those memory locations of the memory for addressing which are associated with the particular parameter. Since some means for addressing the memory must be present in any event, this achieves the selected access of the enabled parameter set in a simple manner.

DESCRIPTION OF THE DRAWINGS

The single figure is a schematic block diagram of a medical device constructed in accordance with the principles of the present invention, in the form of a heart pacemaker.

DESCRIPTION OF THE PREFERRED EMBODIMENTS

The invention will be explained with reference to the drawing in the embodiment of a heart pacemaker, which is generally referenced at 1. The pacemaker 1 has a schematically indicated housing 2, which is hermetically tight and is suitable for implantation in the body of a patient. An electrode 3 leads from the housing 2 to the heart 4 of a patient, and is attached in a ventricle, preferably the right ventricle, accessible through the vein system. The heart pacemaker 1 is preferably operable in the VVI mode.

Only those components of the pacemaker 1 necessary to explain the invention will be discussed. These include a microprocessor 5, to which a read-only memory (ROM) 6 and a write-read memory (RAM) 7 are connected via respective data lines 8 and 9 and respective address lines 10 and 11. A line 13 for switching the RAM 7 from the write mode to the read mode and vice versa is also connected between the RAM 7 and the microprocessor 5. A program with which all functions of the pacemaker 1 are controlled is stored in the ROM 6. Therefore, when it is stated below that the microprocessor 5 executes a specific function, this is understood to mean that the microprocessor 5 becomes active for the execution of the respective function upon the execution of the program stored in the ROM 6, with utilization of data contained in the RAM 7 and using data supplied to it in some other way, for example, via the other input connections.

A crystal 14, connected to the microprocessor 5, generates the clock signals required for the operation of the microprocessor, and also represents the time reference for the Operation of the pacemaker 1.

The microprocessor 5 has input/output connections, generally referenced at 15, which include a plurality of channels 16, 17 and 18.

The channel 16 supplies the heart 4 with stimulation pulses when necessary. The channel 16 therefore includes a stimulation pulse generator 20, having an output line connected to the electrode 3. The stimulation pulse generator 20 can be activated for generating an electrical stimulation pulse via a line 22 connected to a corresponding output of the microprocessor 5. Digital data relating to the shape of the stimulation pulses, for example their amplitude and duration, proceed from the microprocessor 5 via a line 23 to a digital-to-analog interface 24, which supplies the stimulation pulse generator 20 with analog control signals corresponding to the digital data via a control line 25. These control signals set the stimulation pulse generator 20 so that it generates stimulation pulses having the desired shape, as needed.

The channel 17 includes a signal editing circuit 27, also connected to the electrode 3 via an input line 26. The signal editing circuit 27 filters and amplifies an electrical signal taken from the heart 4 via the electrode 3 which corresponds to the activity of the heart. The signal editing circuit 27 therefore includes a filter 27a and an amplifier 27b. The edited signal proceeds from the output of the signal editing circuit 27 to an analog-to-digital converter 28. From the converter 28, the digital data proceed via a line 29 to a corresponding input of the microprocessor 5. These digital data correspond to the curve of the electrical signal which is present at the output of the signal editing circuit 27, which in turn reflects the electrical activity of the heart 4. The microprocessor 5 is connected to a digital-to-analog interface 31 via a line 30, which forwards the digital data supplied to it from the microprocessor 5 to the signal editing circuit 27 as corresponding analog signals via a control line 32. The digital data, or the corresponding analog signals, serve the purpose, for example, of setting the gain of the amplifier 27b, or completely inhibiting the amplifier 27b.

The digital data which are supplied to the microprocessor 5 via the line 29 are analyzed by the microprocessor 5 to determine whether indications of the occurrence of a natural heartbeat are contained in the electrical signal which corresponds to the activity of the heart 4. When the microprocessor 5 detects a natural heartbeat, or when it activates the stimulation pulse generator 20 via the line 22 to generate a stimulation pulse, the microprocessor 5 begins to operate as a counter, and thus begins to count a plurality of clock pulses derived from the oscillation of the crystal 14. This plurality corresponds to time interval which is adjustable between an upper limit and a lower limit. The time interval which is set defines the stimulation repetition rate with which the heart 4 is stimulated in the absence of natural heartbeats. If no data which the microprocessor 5 detects as a natural heartbeat proceed to the microprocessor 5 via the channel 17 during this time interval, the microprocessor 5 activates the stimulation pulse generator 20 via the line 22 after the expiration of the time interval. Following the generation of a stimulation pulse, the microprocessor 5 again begins to count a plurality of clock pulses corresponding to the time interval which defines the stimulation frequency. If, by contrast, the microprocessor 5 now detects a natural heartbeat during this interval, it aborts the counting process if a further time interval, known as the refractory time, has expired, and begins the counting process anew.

The time interval which defines the stimulation repetition rate is adjustable between, for example, 400 and 2,000 ms. The refractory time is shorter than this time interval, and is adjustable to last between approximately 250 and 450 ms. The refractory time is in turn divided into an absolute refractory time, having a fixed duration of, usually, 125 ms, and a relative refractory time which includes the remaining portion of the total refractory time that has been set. The refractory time begins to run simultaneously with the time interval that defines the stimulation repetition rate, and is calculated by the microprocessor 5 during the course of the same counting process which serves for calculating the time interval that defines the stimulation repetition rate. The amplifier 27b of the signal editing circuit 27 in the channel 17 is completely inhibited during the absolute refractory time, which is achieved by means of an appropriate control signal from the microprocessor 5 to the amplifier 27b via the line 30, the digital-to-analog interface 31, and the control line 32. As a consequence of the complete inhibition of the amplifier 27b, no detection of any kind is possible with the microprocessor 5 for the duration of the absolute refractory time. After the expiration of the absolute fractory time, the microprocessor 5 re-activates the amplifier 27b, so that it is capable of detecting natural heartbeats. In contrast to a detection occurring after the expiration of the refractory time, if the microprocessor detects a natural heartbeat during the relative refractory time, it does not abort the counting process for calculating the time interval which defines the stimulation frequency, but instead continues counting and ceases counting with the activation of the stimulation pulse generator 20. After detection of a natural heartbeat, however, the microprocessor 5 again starts the full refractory time. This result in stimulation pulses being generated with the repetition rate defined by the time interval regardless of the occurrence of natural heartbeats, in case of high-frequency disturbances which can lead to incorrect detections. Even when the spontaneous heartbeat repetition rate is so high that the occurrence of natural heartbeats always occurs within the relative refractory time, the generation of stimulation pulses ensues with the stimulation repetition rate defined by the time interval which has been set, until the spontaneous heartbeat repetition rate has returned to a rate below the rate whose period corresponds to the refractory time which has been set. Termination of certain re-entry tachycardia is possible with this method.

The microprocessor 5 is connected to a telemetry circuit 34 via a line 33. A transmission/reception coil 35 is connected to the telemetry circuit 34. The pacemaker 1 is thus able to exchange data with an external programming device 36, having a keyboard 37 and a monitor 38. The programming device 36 is connected via a line 39 to a second telemetry circuit 40, having a transmission/reception coil 41. For data exchange between the implanted pacemaker 1 and the programming device 36, the transmission/reception coil 41 of the telemetry circuit 40 is positioned on the body surface of the patient in whom the pacemaker 1 has been implanted so that it is inductively coupled with the transmission/reception coil 35 of the pacemaker 1. The data contained in the ROM 6 and in the RAM 7 can thus be supplied to the programming device 36 for checking the data or for modifying the data. It is also possible to supply modified or additional data to the RAM 7 via the programming device 36.

Data is supplied to the microprocessor 5 via a channel 18 corresponding to the physical activity of the patient in whom the pacemaker 1 is implanted. This data is used, on the basis of the program stored in the ROM 6, to permit the microprocessor 5 to adapt the stimulation intensity, such as the time interval corresponding to the desired heartbeat rate, to the physical activity of the patient. For this purpose in the embodiment of FIG. 1, a piezoelectric pressure sensor 42 is attached to a wall of the housing 2 so as to be in indirect mechanical contact with the patient. During physical activity of the patient, mechanical oscillations in the body of the patient arise due to movement of the muscles and connecting tissue, which propagate in the body of the patient as pressure waves and are monitored by the piezoelectric sensor 42, which converts the pressure waves into electrical signals. These signals have an amplitude which increases with increasing physical activity. The signals proceed via a line 43 to a signal editing circuit 44, which contains a filter 44a and an amplifier 44b. The output signal of the signal editing circuit 44 proceeds via a line 45 to an analog-to-digital converter 46 which may be, for example, an 8-bit converter. The digital output signals of the converter 46 proceed via a line 47 to the microprocessor 5.

The microprocessor 5 is connected via a line 48 to a digital-to-analog interface 49, which forwards the digital data supplied to it by the microprocessor 5 to the signal editing circuit 44 as corresponding analog signals via a control line 50. The digital data and the analog signals corresponding thereto serve the purpose, for example, of setting the gain of the amplifier 44b or of varying the characteristic of the filter 44a. Dependent on the chronological curve of the signal derived from the piezoelectric sensor 42 (or the corresponding digital data) the microprocessor 5 varies the time interval which defines the stimulation rate such that, in a manner similar to that disclosed in U.S. Pat. No. 4,428,378, this time interval is shortened with increasing physical activity. This is accomplished between a lower limit (resting phase) and an upper limit (maximum heartbeat rate) which are selected corresponding to the requirements of the patient. Corresponding data are telemetrically entered in the RAM 7.

Among the data stored in the RAM 7 are data which define:

(a) the chronological duration of the stimulation pulses;
(b) the amplitude of the stimulation pulses;
(c) the sensitivity of the signal editing circuit 27 of the channel 17;
(d) the sensitivity of the signal editing circuit 44 of the channel 18;
(e) the upper limit value of the stimulation frequency;
(f) the lower limit value of the stimulation frequency;
(g) the duration of the refractory times; and
(h) a heartbeat rate corresponding to reduced physical activity.

The RAM 7 has a field of 8 bits. One data word having a length of 8 bits can thus be stored for each of the parameters (a) through (h).

The parameters recited in (a) through (h) form a parameter set which influences the interaction of the heart pacemaker 1 with the body of the patient, and in particular with the heart 4 of the patient. A total of six different parameter sets can be stored in the RAM 7 The parameters (a) through (h) are stored at addresses XXX000 through XXX111 for each parameter set. The individual parameter sets are stored under the addresses 000XXX through 101XXX. The symbol X denotes that a 0 or a 1 can be present at this bit location.

For example, the upper limit value of the stimulation frequency associated with the fourth parameter set will be stored at the address 011100.

Which of the parameters can be fetched, i.e. can be addressed by the microprocessor 5 via the address line 11 s that the microprocessor 5 can access the data with respect to the individual parameters (a) through (h), is initially dependent on data which proceed to the microprocessor 5 from a real-time clock 51 via a line 52. For example, during a time from 0900 hours through 2100 hours, the microprocessor 5 addresses the first data set under the addresses 000XXX which, with respect to the individual parameters (a) through (h), contain data corresponding to the requirements of the patient during which the patient has increased physical activity. During the time from 2300 hours through 0600 hours, the microprocessor 5 can only address the second parameter set under the addresses 001XXX, the second parameter set being matched to the requirements of a sleeping patient. In the remaining time spans from 0600 hours through 0900 hours and from 2100 hours through 2300 hours, only the third parameter set under the address 010XXX is enabled for addressing. The third parameter set is adapted to the requirements of the patient given limited physical activities.

The fourth parameter set, stored under the address 011XXX, contains parameters (a) through (h) which correspond to the requirements of the patient if the patient has no physical activity during the day, i.e. during a time from 0600 hours through 2300 hours, for example if the patient is taking a mid-day nap. If either the first or the third parameter set is enabled for addressing, the microprocessor 5 compares the heart beat rate of the patient, or the stimulation rate if stimulation is taking place, to the limit value of the heart beat rate conforming to parameter (h) which corresponds to a limited physical activity on the part of the patient. If this limit value is downwardly transgressed for a defined time, for example 15 minutes, the microprocessor 5 accesses the fourth parameter set, regardless of whether a different parameter set, such as the first or third parameter set, would otherwise be controlling according to the data supplied from the real-time clock 51. The other parameter sets are not enabled or addressing during this time. As soon as the heart beat rate or stimulation rate again exceeds the limit value, the fourth parameter set is inhibited, and the parameter set which would be normally controlling according o the data from the real-time clock 51 is enabled.

The fifth parameter set, stored under the address 100XXX, is adapted to the requirements of a bedridden, sick patient. In the event of such sickness, this a parameter set may be telemetrically enabled for addressing by means of an operating device 53 available to the patient. The operating device 53 includes a telemetry circuit 64, a transmission coil 55 connected thereto, and a push button 56 connected o the telemetry circuit 54. When the push button 56 is actuated, a signal which causes the microprocessor 5 to access the fifth parameter set proceeds to the pacemaker 1. The first four parameter sets are inhibited until the fifth parameter set is again inhibited by a subsequent actuation of the push button 56. When this occurs, the parameters set which is controlling in accordance with the criteria set forth above is enabled for addressing.

The sixth parameter set, which can be reached under the address 101XXX, contains data for diagnostic purposes which allow the attending physician to evaluate the interaction of the heart pacemaker 1 with the patient, when the patient appears for a routine appointment, or because of the occurrence of symptoms. The physical can enable this parameter set by appropriate actuation of the keyboard 37 of the programming device 36. The sixth parameter set is then enabled for addressing for a defined time span, for example 10 minutes, which the microprocessor 5 calculates on the basis of the data supplied thereto from the real-time cock 51. All other parameter sets are inhibited during this time span. After the expiration of the defined time span, that parameter set which would be controlling according to the above-described criteria is again enabled for addressing.

The programming device 36 also permits the attending physician to enable an arbitrary set of the first five parameter sets for addressing for diagnostic purposes. The programming device 36 also permits the attending physician to modify data with respect to the parameters (a) through (h) contained in the parameter sets.

Data which are not allocated to any of the parameter sets, and which the microprocessor 5 can access at any time, can be stored in the RAM 7 under the addresses 110000 through 111111. Such data, which can be entered with the programming device 36, may be data serving for patient identification.

A plurality of functions is executed by an appropriately programmed microprocessor in the heart pacemaker described above. It is also possible to use conventionally constructed control logic, however, instead of the microprocessor 5.

The invention has been explained above in the embodiment of a heart pacemaker, however, it will be understood by those skilled in the art it can be used in any type of medical device for stimulating and/or monitoring physiological function of a patient.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical device comprising:
   a housing having a size adapted for implantation in the body of a patient;
   means adapted for interacting with the body of said patient with respect to a physiological function of the patient;
   control means in said housing and electrically connected to said means adapted for interacting, for defining the interaction of said means adapted for interacting on the basis of a parameter set;
   a memory in said housing containing a plurality of different parameter sets each parameter set comprising values of a plurality of individual parameters matched to a specific set of physiological conditions of said patient with each set of conditions requiring a different interaction with said patient by said means for interacting, and each of said parameter sets being stored as a set at a specific Address of said memory;
   said control means including means for fetching one of said parameter sets at a time for use by said control means; and
   switch means connected to said control means for enabling only the address of a parameter set matched to current conditions, said switch means including pacemaker wearer-operated means for selecting an address which is to be enabled, said pacemaker wearer-operated means being an external unit and further including means for telemetrically communicating between said control means in said housing and said external unit.

2. A medical device as claimed in claim 1, wherein said switch means includes a real-time clock and wherein said switch means is controlled by said real-time clock for enabling fetching of respective parameter sets based on the time of day.

3. A medical device as claimed in claim 1 wherein said human-operated unit further includes human-actuated means for subsequently unihibiting fetching of a previously selected parameter set.

4. A medical device as claimed in claim 1 wherein said switch means includes means for automatically inhibiting fetching of a previously selected parameter set after the expiration of a defined time interval.

5. A medical device as claimed in claim 1 wherein said switch means is a switch means for enabling fetching of a parameter set dependent on the intensity of said physiological function.

6. A medical device as claimed in claim 1 wherein said means adapted for interacting with the body of a patient includes means adapted for detecting physiological events in said patient.

7. A medical device as claimed in claim 1 wherein said means adapted for interacting with the body of a patient includes means adapted for stimulating physiological events in said patient.

8. A medical device as claimed in claim 1 wherein said means adapted for interacting with the body of a patient is a heart pacemaker including means for monitoring the electrical activity of the heart of said patient and means for stimulating heart activity in said patient with electrical stimulation pulses.

* * * * *